United States Patent [19]

Christidis et al.

[11] 4,074,054
[45] Feb. 14, 1978

[54] IMIDAZOLES AND 2-ALKYL IMIDAZOLES AND METHOD FOR THEIR MANUFACTURE

[75] Inventors: Yani Christidis, Paris; Dominique Depernet, Stains, both of France

[73] Assignee: Nobel Hoechst Chimie, Puteaux, France

[21] Appl. No.: 672,493

[22] Filed: Mar. 31, 1976

[30] Foreign Application Priority Data

Apr. 3, 1975 France .................................. 75 10510

[51] Int. Cl.$^2$ .......................................... C07D 233/58
[52] U.S. Cl. .................................................. 548/335
[58] Field of Search ........................ 260/309; 548/335

[56] References Cited

U.S. PATENT DOCUMENTS

| 2,801,243 | 7/1957 | Hanslick et al. | 260/309 |
| 2,905,692 | 10/1959 | Paleveda et al. | 260/309 |
| 3,361,755 | 1/1968 | Green | 260/309 |
| 3,715,365 | 2/1973 | Schulze | 260/309 |

FOREIGN PATENT DOCUMENTS

| 183,588 | 4/1907 | Germany | 260/309 |
| 2,360,175 | 6/1975 | Germany | 260/309 |
| 930,090 | 7/1963 | United Kingdom. | |

OTHER PUBLICATIONS

Groggins Unit Processes in Organic Synthesis 5th ed. p. 680, N.Y., McGraw-Hill 1963.
Fieser et al. Reagents for Organic Synthesis vol. 1, pp. 413–414, N.Y., Wiley, 1967.
Hofmann Imidazole and Its Derivatives Part I, pp. 33–39 N.Y., Interscience, 1953.

*Primary Examiner*—Natalie Trousof
*Attorney, Agent, or Firm*—Karl W. Flocks

[57] ABSTRACT

The method is for manufacturing imidazoles corresponding to the general formula:

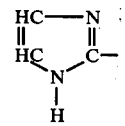

in which R represents hydrogen or an alkyl radical of 1 to 17 carbon atoms. Glyoxal is condensed with an aliphatic aldehyde and ammonia, in a hydroalcoholic medium at a pH comprised between 6 and 8. The glyoxal is in the form of its bisulfite combination and the ammonia being supplied by an ammonium salt of a weak acid.

5 Claims, No Drawings

IMIDAZOLES AND 2-ALKYL IMIDAZOLES AND METHOD FOR THEIR MANUFACTURE

BACKGROUND OF THE INVENTION

1. Field of the Invention

The present invention relates to a method of manufacturing imidazole and 2-alkyl imidazoles and notably 2-alkyl imidazoles with a long alkyl chain of $C_4$ to $C_{17}$ as well as the new 2-alkyl imidazoles obtainable by this method.

The imidazoles manufactured by the method according to the invention correspond to the general formula:

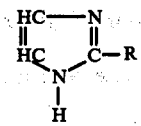

in which R represents hydrogen or an alkyl radical of 1 to 17 carbon atoms.

2. Description of the Prior Art 2-alkyl imidazoles are usually prepared by dehydrogenation of 2-alkyl imidazolines at a high temperature in the presence of hydrogenation catalysts, the 2-alkyl imidazolines being themselves obtained from ethylenediamine and fatty acids, or from derivatives of fatty acids (nitriles, esters, chlorides).

Another method of obtaining 2-alkyl imidazoles consists of decarboxylating, by heating in the presence of catalysts, imidazole-4,5-dicarboxylic acids suitably substituted at the 2 position, themselves obtained by the reaction of tartric acid dinitrate with ammonia and an aldehye.

These methods of manufacture are relatively long and complicated to operate since they necessitate the preparation of an intermediate compound.

It is also known that imidazoles can be prepared by reaction of alpha-hydroxy ketones such as acetoin, benzoin, or furoin, with an aldehyde in the presence of ammoniacal copper acetate solutions. This method gives good results with the lower aldehydes, that is to say having up to four carbon atoms. On the other hand, with higher aldehydes (more than 4 carbon atoms) which are known as being less reactive, the cyclisation does not take place and the majority of the aldehyde is uncondensed or even secondary reactions occur so that the yields are nil or negligible.

It is the same in the case of the preparation of imidazoles by the so-called RADZISZEWSKI method which consists of reacting together, ammonia, glyoxal and a suitable aldehyde (see among others German patent application No. 1,903,614). Inspite of these improvements or modifications intended to produce more satisfactory results, this method does not permit the obtaining of good yields of 2-alkyl imidazoles with a long alkyl chain. Thus it has been proposed to use ammonia in alcoholic solution, or to carry out the condensation in a glacial acetic acid medium or even in an aqueous medium with, as a source of ammonia, ammonium salts of strong acids such as ammonium sulfate (see U.S. Pat. Nos. 3,715,365 and 3,361,755). However these procedures do not permit the condensation of all aldehydes and, in particular, aldehydes having 5 to 18 carbon atoms.

OBJECTS AND SUMMARY OF THE INVENTION

It is an object of the present invention to provide a method for the manufacture of 2-alkyl imidazoles with a long alkyl chain which is relatively simple and uncomplicated.

It is another object of the invention to provide an improved method for the preparation of 2-alkyl imidazoles with an alkyl chain having 4 to 17 carbon atoms.

It is also an object of the invention to provide a simple and profitable method for manufacturing imidazoles of the general formula:

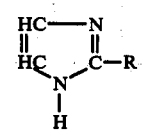

in which R represents hydrogen or an alkyl radical having 1 to 17 carbon atoms.

Other objects and advantages of the method according to the invention will become apparent from the description which follows.

According to the invention there is provided a method for manufacturing imidazoles corresponding to the general formula:

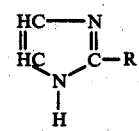

in which R represents a hydrogen or an alkyl radical of 1 to 17 carbon atoms, by the condensation of glyoxal with an aliphatic aldehyde and ammonia, in which method the condensation takes place in a hydroalcoholic medium at a pH comprised between 6 and 8, the glyoxal being in the form of its bisulfite combination and ammonia being supplied by an ammonium salt of a weak acid.

The method according to the invention permits notably the condensation of aliphatic aldehydes with a branched chain obtained by the "OXO" synthesis from isobutylene and/or propylene.

As in the Radziszewski method, by starting from an aldehyde of the formula R-CHO, an imidazole of the above formula is obtained in which the chain represented by R contains 1 carbon less than the starting aldehyde.

More precisely, the aldehyde is condensed between 50° and 90° C, at a pH comprised between 6 and 8, and if necessary under nitrogen, for a longer or shorter time according to its reactivity, with a bisulfite combination of the glyoxal and an excess of an ammonium salt of a weak acid in hydroalcoholic medium. The 2-alkyl imidazole is then isolated by conventional methods which can vary according to the nature of the aldehyde, then if necessary purified by vacuum distillation or recrystallisation.

The proportions of the reactants to be used are about 1 mole of aldehyde and 2.6 to 4 moles of ammonia in the form of a combination with a weak acid per mole of glyoxal bisulfite combination.

A part of the weak acid ammonium salt may also be replaced by ammonia provided that a part of the latter is added gradually in the course of the reaction so as to maintain the pH of the medium between 6 and 8 and to compensate for the consumption of $NH_4^+$.

Of course, the method according to the invention applies not only to the synthesis of 2-alkyl imidazoles with a long alkyl chain, but also to the synthesis of 2-alkyl imidazoles with a short alkyl chain or to the synthesis of imidazole itself.

The aldehydes usable are all aliphatic aldehydes with a straight or branched chain up to $C_{18}$, like for example, oenanthol (or heptanal). As has been stated above, the method according to the invention applies particularly well to aliphatic aldehydes obtained by the "OXO" synthesis from isobutylene and/or propylene such a valeraldehyde $CH_3(CH_2)_3$—CHO, isovaleraldehyde or 3-methyl butanal $(CH_3)_2$—CH—$CH_2$—CHO, pivalylaldehyde or 2,2-dimethylpropanol:

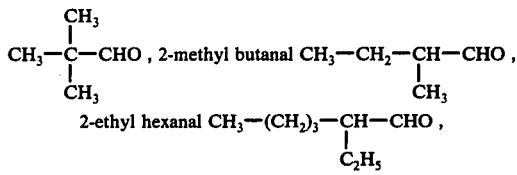

or their mixtures as well as mixtures of aldehydes known by the name of isooctylaldehyde, isononylaldehyde, isodecylaldehyde, isotridecylaldehyde, isocetylaldehyde and isooctacdecylaldehyde. Whilst the known 2-alkyl imidazoles are solids, those obtained from the "OXO" synthesis, when they have a sufficiently branched structure, are liquid 2-alkyl imidazoles which do not crystallise, which, for certain applications, can offer advantages. These compounds constitute new industrial products.

The bisulfite combination of glyoxal may be used in any form, anhydrous, hydrated or in solution, if necessary prepared in situ before the condensation. This combination is normally used in the form of the hydrate of the sodium salt $(CH(OH)\ SO_3Na)_2, H_2O$, but it is also possible to employ a salt of another alkali metal or of ammonium.

As the ammonium salt of a weak acid, a salt permitting the obtaining of a pH of 6 to 8 in the reaction medium is employed, since it is indispensable for the medium not to become too acidified in the course of the condensation, which excludes the use of ammonium salts of strong acids. The carbonates and bicarbonates of ammonium are particularly suitable, but it is also possible to use, for example, as the weak acid, sodium acid sulfite, the second acidity of the sulfurous acid being a weak acidity. It then suffices to prepare in situ a sodium and ammonium sulphite by the addition of ammonia to acid sodium sulfite.

The alcohol used as solvent is for the purpose of facilitating the solution of the aldehydes and of permitting regularisation of the reaction temperature and it must be at least partly miscible with water. Isopropanol and isobutanol are particularly advantgeous since they can if necessary be removed after the condensation by azeotropic stripping with water.

The separation of the 2-alkyl imidazole formed is effected by very various processes known in themselves which essentially depend upon the solubility and the physical state of this compound.

The 2-alkyl imidazoles obtained by the method according to the invention may be used in all known applications of 2-alkyl imidazoles, such as anti-static agents, heat stablisers for polymers, fuel additives and particularly as an anti-corrosion agents for steel, brass or copper parts.

DESCRIPTION OF SPECIFIC EMBODIMENTS

The following examples are given purely by way of illustration are not to be regarded as limiting the invention in any way.

EXAMPLE 1

The following are subjected to reflux boiling under nitrogen:

(80°–85° C)
Isovalderaldehyde: 34.5 g (0.4 mol.)
Bisulfite combination of glyoxal (hydrate): 113.6 g (0.4 mol.)
Ammonium carbonate: 91.5 g (0.8 mol.)
Water: 300 ml
Isopropanol: 50 ml The pH of the reaction medium is in the neighbourhood of 7 throughout the duration of the boiling (7 hours). The isopropanol is distilled off in the form of its aqueous azeotrope, then the unreacted aldehyde (6.3 g) is stripped by the steam; the solution is made alkaline with a 10% soda solution (pH 10). After cooling, 19.4 g of 2-(2-methyl propyl) imidazole are obtained. Taking into account the recovery of isovaleraldehyde, the yield is 51.7%. The product is purified by dissolving in aqueous HCl approximately 3N, then by filtration and neutralisation with soda (yield 72.5%).

Nitrogen analysis (Dumas) Calculated: 22.6%. Found: 21.8%.

Acidimetry analysis in a non-aqueous medium 97% melting point 118° C

EXAMPLE 2

The following are heated by reflux boiling:
2-ethyl hexanal: 51.2 g (0.4 mol.)
Bisulfite combination of glyoxal (hydrate): 113.6 g (0.4 mol.)
Ammonium carbonate $(NH_4)_2CO_3, H_2O$: 62 g (0.54 mol.)
Water: 350 ml
Isopropanol: 150 ml After 7 hours, it is cooled, then the isopropanol is distilled off in the form of its aqueous azeotrope; the unreacted 2-ethylhexanal is then stripped by the steam. 16.5 g of aldehyde are thus recovered. By the addition of acetone and cooling, crystals are obtained; dry weight 38 g.

Taking into account the 2-ethyl hexanal recovered, the yield is 85% with respect to the aldehyde.

Melting point of the 2-(1-ethyl pentyl) imidazole obtained: 66.5° –67° C.

EXAMPLE 3

Into a round bottomed flask is placed:

Bisulfite combination of glyoxal (hydrate): 113.6 g (0.4 mol.)
Isopropanol: 150 ml It is purged with nitrogen and then there is added:

Isooctylaldehyde (from the OXO synthesis): 51.2 g (0.4 mol.)

then a solution of ammonium bicarbonate: 95 g (1.2 mol.)
in water: 150 ml

It is heated gradually up to 50° C; it is kept at this temperature for 6 hours, then the heating is increased until reflux boiling (80° C) which is maintained for 16 hours.

As in the foregoing Examples, the isopropanol is distilled, then the unreacted aldehyde is extracted with the steam (5g). The solution is then made alkaline with a soda solution, then extracted with methylene chloride. After evaporation, 48 g of yellow liquid are obtained, namely a yield of 80% of crude product, taking into account the recovered aldehyde. By distillation, 41 g of yellow liquid are obtained passing over at 120°-126° C under 0.02 mm pressure of mercury. Yield of distilled product with respect to the aldehyde 68.5%

Proportion of nitrogen (Dumas): calculated: 16.85%. found: 16.6%.

Acidimetric titration: 97% of theory

EXAMPLE 4

The following was heated to reflux boiling for 10½ hours:

Isononylaldehyde (from OXO synthesis): 57 g (0.4 mol.)
Bisulfite combination of glyoxal (hydrate): 113.6 g (0.4 mol.)
Ammonium carbonate: 62 g (0.54 mol.)
Water: 420 ml
Isopropanol: 150 ml Then the isopropanol is distilled, and the solution concentrated to 250 ml and steam stripped. By extraction from the distillate, 13 g of isononylaldehyde are recovered. After steam stripping, the mother liquor is cooled, made alkaline and then extracted with toluene; the organic phase is concentrated and then distilled. 25.5 g of viscous yellow product distilling at 155° C under 4 mm of mercury, are obtained. The yield with respect to the aldehyde consumed is 46%.

Proportion of nitrogen (Dumas): calculated: 15.54%. found: 14.6%.

Acidimetric titration in non-aqueous medium: 91.6% of theory

EXAMPLE 5

Into a round bottomed flask under nitrogen are placed:

Isotridecylaldehyde (from the OXO synthesis): 79.4 g (0.4 mol.)
Bisulfite combination of glyoxal (hydrate): 113.6 g (0.4 mol.)
Ammonium bicarbonate: 127 g (1.6 mol.)
Water: 150 ml
Isopropanol: 150 ml The solution is heated to reflux boiling which is maintained for 22 hours; during the operation the pH remains at 6. After removal of the solvents, the unreacted aldehyde is recovered. The yield is 41.7% of compound distilling at 145°-155° C under 0.05 mm of mercury, whose composition corresponds substantially with the desired product.

EXAMPLE 6

The procedure is as in Example 3 with:
Isooctadecylaldehyde (from OXO synthesis): 107 g (0.4 mol.)
Bisulfite combination of glyoxal: 113.6 g (0.4 mol.)
Ammonium bicarbonate: 127 g (1.6 mol.)
Water: 150 ml
Ispropanol: 150 ml There is recovered, by distillation of the crude product still containing aldehyde, 39 g of aldehyde and 31 g of the imidazole distilling at 135°-155° C under 0.02 mm of mercury, namely a yield of 40.8%.

EXAMPLE 7

By way of comparison, a run was carried out of the condensation of 2-ethyl hexanal with glyoxal and ammonium sulfate. To this end, it was heated to reflux boiling under nitrogen for 7 hours.

Glyoxal 53% solution: 55 g (0.5 mol.)
2-ethyl hexanal: 64 g (0.5 mol.)
Ammonium sulfate: 68 g (0.515 mol.)
Water: 100 ml
Isobutanol 100 ml It was not possible to establish, in the reaction products, the presence of isolatable amounts of 2(1-ethyl pentyl) imidazole and the majority of the 2-ethyl hexanal was recovered intact.

An attempt to condense with ammonium sulfate by using the glyoxal bisulfate instead of the glyoxal gave rise a release of $SO_2$.

Hence it is not possible to use, for the condensation, ammonium sulfate when a relatively long alkyl chain aldehyde is used in the reaction.

EXAMPLE 8

The following are heated with stirring under nitrogen:

| | |
|---|---|
| Water | 100 ml |
| Isopropanol | 100 ml |
| Isovaleraldehyde | 86 g (1 mole) |
| 20 % aqueous ammonia solution | 85 g (1 mole) |
| Ammonium bicarbonate | 79 g (1 mole) |
| Bisulfite combination of glyoxal (hydrate) | 284 g (1 mole) |

The solution is heated for 1 hour at 60° C, then drop by drop 170 g of 20% aqueous ammonia solution (2 moles) are added in 1 hour. It is kept for 7 hours at 90° C, then cooled, and the organic layer is separated and run into 500 ml of water containing 12 g of soda. The precipitate was filtered, washed with water and dried. 75 g of dry, white, product were obtained, namely a yield of 60.5% with respect to the starting aldehyde.

| | MP = 127 - 128° C | | |
|---|---|---|---|
| Elementary analysis: | C | H | N |
| calculated % | 67.7 | 9.74 | 22.56 |
| found % | 67.3 | 9.6 | 22.6 |

The IR and NMR spectra confirm the absence of aldehyde and the presence of an imidazole ring.

EXAMPLE 9

Under nitrogen at 60° C there are heated:

| | |
|---|---|
| Water | 300 ml |
| Isopropanol | 100 ml |
| Sodium bisulfite at 40% | 260 g (1 mole) |
| Isovaleraldehyde | 86 g (1 mole) |
| Bisulfite combination of glyoxal (hydrate) | 284 g (1 mole) |

In 2 hours 340 g of aqueous 20% ammonia solution (4 moles) are added, the pH remaining below 8. After 7 hours boiling under reflux the reaction mixture was filtered, the organic phase separated after cooling was run into 500 ml of water containing 12 g of soda.

56 g of dry product were obtained, namely a yield of 45% with respect to the starting aldehyde.

| | MP = 128 – 129° C | | |
|---|---|---|---|
| Acidimetric titration | | 99.6% of theory | |
| Elemental analysis: | C | H | N |
| Calculated % | 67.7 | 9.74 | 22.56 |
| Found % | 67.6 | 9.7 | 22.7 |

EXAMPLE 10

The bisulfite combination of glyoxal was prepared by adding 580 g of aqueous 40% glyoxal solution (4 moles) to a solution of 352 g of soda (8.8 moles) and 563 g of sulfur dioxide (8.8 moles) in 800 ml of water. It is left to digest for 2 hours, then 61 g (1 mole) of aqueous 28% ammonia solution added, then 400 ml of isopropyl alcohol and 1260 g (16 moles) of ammonium bicarbonate. It is brought to 40° C and then 344 g (4 moles) of isovaleraldehyde added under nitrogen. After refluxing for 16 hours, it is filtered hot, then cooled, the organic phase is separated and run into 2000 ml of iced water containing 48 g of soda. The precipitate is filtered, washed with water and dried. 268 g of dry product were obtained namely a yield of 54% with respect to the starting aldehyde:

| | MP = 129 – 130° C | | |
|---|---|---|---|
| Acidimetric titration | | 98% of theory | |
| Elemental analysis: | C | H | N |
| Calculated % | 67.7 | 9.74 | 22.56 |
| Found % | 67.6 | 9.7 | 22.5 |

EXAMPLE 11

A mixture of 300 ml of water, 100 ml of isopropanol, 284 g (1 mol) of the bisulfite combination of glyoxal in the form of hydrate, and 316 g (4 moles) of ammonium bicarbonate was brought to 40° C, then 114 g (1 mole) of oenanthol was added.

After 20 hours refluxing, the organic phase separated was washed with 250 ml of N aqueous soda solution, then dissolved in methylene chloride. After this solution was washed with water and the solvents evaporated, the solid was taken up in 500 ml of 4N aqueous hydrochloric solution. By making the solution alkaline, a precipitate was obtained which was washed and dried. Dry weight of 2-hexyl imidazole : 81 g namely a yield of 54% with respect to the starting aldehyde.

The IR and NMR spectra show that the product does not contain aldehyde and includes a imidazole ring.

EXAMPLE 12

For 30 minutes in the cold, a mixture of 100 ml of water, 300 ml of isopropanol, 128 g (1 mole) of 2-ethyl hexanal and 85 g (1 mole) of 20% aqueous ammonia solution was stirred, then 79 g (1 mole) of ammonium bicarbonate added. After having again stirred for 30 minutes, 284 g (1 mole) of the bisulfite combination of glyoxal in the form of hydrate was added, then heated to 60° C and in 1 hour 170 g (2 moles) of 20% aqueous ammonia solution run in.

After 7 hours under reflux, it was cooled, filtered, and the organic phase separated which was run into 700 ml of water containing 7 g of soda. By filtration and drying 114 g of white product (yield 69%) were obtained. The spectra IR and NMR confirmed the expected structure.

EXAMPLE 13

Under reflux for 20 hours, 568 g (2 moles) of the bisulfite combination of glyoxal in the form of hydrate, was heated with 284.5 g (1.76 mole) of 88% isononylaldehyde (OXO synthesis) 600 ml. of water and 200 ml of isopropanol and 632 g (8 moles) of ammonium bicarbonate. After cooling, filtration and separation of the organic phase, the isopropanol is distilled off, 400 ml of methylene chloride added and it is extracted with hydrochloric acid. The solution is made alkaline, extracted with methylene chloride, the solvent removed and the brown oil obtained distilled under 3 mm of mercury. 187 g (yield 52.5%) of yellowish viscous liquid were collected, which on redistillation titrated at 99.5% by acidimetry.

| Elemental analysis: | C | H | N |
|---|---|---|---|
| Calculated % | 73.28 | 11.18 | 15.54 |
| Found % | 73.1 | 11.1 | 15.4 |

It is self-evident that the present invention has only been described in purely explanatory manner and not in any limiting way and that any useful modification can be introduced therein without departing from its scope as defined by the following claims.

We claim:

1. In the process of manufacturing an imidazole of the structural formula:

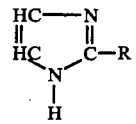

wherein R represents hydrogen or alkyl from 1 to 17 carbon atoms, by condensing glyoxal with an alkanal of 1–18 carbon atoms and ammonia, the improvement comprising effecting said condensation at a pH from 6 to 8 in an aqueous alcoholic medium, said glyoxal being in its bisulphitic combination form and said ammonia being provided as an ammonium salt selected from the group consisting of ammonium carbonate, ammonium bicarbonate, and the ammonium salt resulting from the reaction of ammonia with sodium hydrogen sulfite.

2. The improvement in accordance with claim 1 wherein 2.6 to 4 moles of ammonia are used for about 1 mole of said alkanol and 1 mole of said bisulphitic combination of glyoxal.

3. The improvement in accordance with claim 1 wherein said aqueous alcoholic medium comprises isopropanol or isobutanol.

4. The improvement in accordance with claim 1 wherein said alkanal is selected from the group consisting in isovaleraldehyde, 2-ethyl hexanol, isooctylaldehyde, isononylaldehyde, isotridecylaldehyde, isocetylaldehyde, isooctadecylaldehyde and oenanthol.

5. In the process of manufacturing an imidazole of the structural formula:

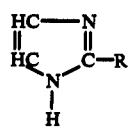

wherein R is alkyl from 1 to 17 carbon atoms, by condensing glyoxal with ammonia and an alkanal of 1–18 carbon atoms resulting from OXO synthesis, the improvement wherein said condensation is carried out at a pH from 6 to 8 in an aqueous alcoholic medium, said glyoxal being in its bisulphitic combination form and said ammonia being provided as an ammonium salt selected from the group consisting of ammonium carbonate, ammonium bicarbonate, and the ammonium salt resulting from the reaction of ammonia with sodium hydrogen sulfite, whereby a liquid, non-crystallizable 2-alkyl imidazole is obtained.

* * * * *